US012383726B2

(12) United States Patent
Löertscher et al.

(10) Patent No.: US 12,383,726 B2
(45) Date of Patent: Aug. 12, 2025

(54) IMPLANT DEVICE WITH MEMS (MICROELECTROMECHANICAL SYSTEM) ACTUATED MEMBRANE

(71) Applicant: International Business Machines Corporation, Armonk, NY (US)

(72) Inventors: Emanuel Marc Löertscher, Bonstetten (CH); Diego Monserrat Lopez, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 421 days.

(21) Appl. No.: 17/446,730

(22) Filed: Sep. 2, 2021

(65) Prior Publication Data

US 2023/0065107 A1    Mar. 2, 2023

(51) Int. Cl.
*A61M 60/441* (2021.01)
*A61M 5/142* (2006.01)
(Continued)

(52) U.S. Cl.
CPC ...... *A61M 60/441* (2021.01); *A61M 5/14276* (2013.01); *A61M 60/122* (2021.01);
(Continued)

(58) Field of Classification Search
CPC .. A61M 2205/0238; A61M 2205/0244; A61M 2205/0272; A61M 2205/0283;
(Continued)

(56) References Cited

U.S. PATENT DOCUMENTS

| 5,025,346 A * | 6/1991 | Tang .................. G03F 7/00 73/DIG. 1 |
| 7,559,926 B1 * | 7/2009 | Blischak ........... A61M 5/14526 604/890.1 |

(Continued)

FOREIGN PATENT DOCUMENTS

| EP | 4395850 A1 | 7/2024 |
| WO | 2023/030933 A1 | 3/2023 |

OTHER PUBLICATIONS

"Notification of Transmittal of the International Search Report and the Written Opinion of the International Searching Authority, or the Declaration", From the International Searching Authority, International application No. PCT/EP2022/073257, International filing date: Aug. 19, 2022, Date of mailing: Dec. 5, 2022, 16 pgs.

(Continued)

Primary Examiner — Pamela M. Bays
(74) Attorney, Agent, or Firm — Yee & Associates, P.C.

(57) ABSTRACT

An implant device having a biointerface. The implant device comprises a cavity and a structure enabling a flow path between the cavity and an environment of the implant device. An actuatable membrane is interposed in the flow path. The device includes a power-generating unit and a control unit, where the latter is connected to the power-generating unit. An electromechanical is connected to both the control unit and the power-generating unit. The electromechanical system includes at least one actuator configured to mechanically contact the membrane. This actuator is permanently attached to the membrane. The control unit and the electromechanical system are jointly configured to cause the electromechanical system to controllably actuate the membrane via at least one actuator to control a transfer of substances between the cavity and the environment through (Continued)

the flow path. The invention is further directed to related operation and fabrication methods.

20 Claims, 7 Drawing Sheets

(51) Int. Cl.
    *A61M 60/122*      (2021.01)
    *A61M 60/268*      (2021.01)
    *A61M 60/508*      (2021.01)
    *A61M 5/145*      (2006.01)

(52) U.S. Cl.
    CPC ........ *A61M 60/268* (2021.01); *A61M 60/508* (2021.01); *A61M 5/14586* (2013.01); *A61M 2205/0244* (2013.01); *A61M 2205/0272* (2013.01); *A61M 2207/00* (2013.01)

(58) Field of Classification Search
    CPC .......... A61M 2205/04; A61M 2207/00; A61M 5/14276; A61M 5/14586; A61M 5/16813; A61M 5/172; A61M 60/122; A61M 60/268; A61M 60/441; A61M 60/508
    See application file for complete search history.

(56) References Cited

U.S. PATENT DOCUMENTS

| | | |
|---|---|---|
| 9,693,894 B2 | 7/2017 | Tai |
| 9,907,906 B2 | 3/2018 | Ordeig |
| 2003/0225360 A1* | 12/2003 | Eppstein ................ A61N 1/044 604/19 |
| 2004/0024382 A1 | 2/2004 | Cho |
| 2005/0238506 A1* | 10/2005 | Mescher ............... F04B 35/045 417/413.1 |
| 2006/0041183 A1* | 2/2006 | Massen ............... A61M 60/454 623/13.13 |
| 2006/0206049 A1 | 9/2006 | Rodgers |
| 2006/0280906 A1* | 12/2006 | Trentacosta ........... B01D 69/02 428/137 |
| 2018/0214634 A1 | 8/2018 | Neftel |
| 2023/0047856 A1* | 2/2023 | Dehé .................... H04R 17/005 |

OTHER PUBLICATIONS

Meng, et al., "MEMS-enabled Implantable Drug Infusion Pumps for Laboratory Animal Research, Preclinical, and Clinical Applications", Advanced Drug Delivery Reviews, Elsevier, Aug. 19, 2012, 11 pgs., <http://dx.doi.org/10.1016/j.addr.2012.08.006>.

Pirmoradi, et al., "On-Demand Controlled Release of Docetaxel from a Battery-less MEMS Drug Delivery Device", Lab on a Chip, Jun. 23, 2011, 11, 2744, 9 pgs., DOI: 10.1039/c11c20134d.

Song, et al., "Engineering Implantable Microfluidic Drug Delivery Device for Individualized Cancer Chemotherapy", Proceedings of the International Conference on Biomedical Electronics and Devices (Biodevices-2015), 2015, 7 pgs., Lisbon, Portugal, DOI: 10.5220/0005202900370043.

Tu, et al., "An Implantable MEMS Micropump System for Drug Delivery in Small Animals", Biomedical Microdevices, Jan. 2021, 30 pgs., DOI: 10.1007/s10544-011-9625-4.

Farina et al. "Cell encapsulation: Overcoming barriers in cell transplantation in diabetes and beyond", Advanced Drug Delivery Reviews, Jan. 15, 2019, pp. 92-115, vol. 139.

Kim et al. "A High-Aspect-Ratio Comb Actuator Using UV-LIGA Surface Micromachining and (110) Silicon Bulk Micromachining", Journal of Micromechanics and Microengineering, Feb. 18, 2002, 9 pages, vol. 12, No. 2.

Krawczyk et al. "Electrogenetic Cellular Insulin Release for Real-Time Glycemic Control in Type 1 Diabetic Mice", Science, May 29, 2020, pp. 993-1001, vol. 368, Issue 6494.

Lee et al. "Implantable batteryless device for on-demand and pulsatile insulin administration", Nature Communications, Apr. 13, 2017, 10 pages.

Puebla-Hellmann et al. Functional Nanopores: A Solid-state Concept for Artificial Reaction Compartments and Molecular Factories, CHIMIA International Journal for Chemistry, Jun. 2016, pp. 432-438, vol. 70, No. 6.

Puebla-Hellmann et al. "Metallic Nanoparticle Contacts for High-Yield, Ambient-Stable Molecular-Monolayer Devices", Nature, Jul. 2018, pp. 232-235, vol. 559, No. 7713.

Santos et al. "Combinatorial Strategy for Studying Biochemical Pathways in Double Emulsion Templated Cell-Sized Compartments", Advanced Materials, 2020, 13 pages, vol. 32.

\* cited by examiner

IMPLANT DEVICE WITH MEMS (MICROELECTROMECHANICAL SYSTEM) ACTUATED MEMBRANE

BACKGROUND

The invention relates in general to biocompatible implant devices, methods of operating such devices, and methods of fabrication of such devices. In particular, it is directed to an implant device having a membrane actuated via an electromechanical system (for example, a micro electromechanical system) to control a transfer of substances between the device and its environment, where the membrane may possibly be used to mechanically stimulate this environment.

With advances in medical knowledge, biocompatible materials, tailored manufacturing capabilities, and miniaturized hardware, an increasing number of implant devices are now being developed. While the first dental implants date back to at least 2000 BC, more complex implants (for example, replacing defective joints or bones including artificial knee or hip joints) became possible thanks to advances in modern medicine and manufacturing. Such implants require more invasive surgery, carry a high risk of inflammation, and can cause severe reactions (also called "implant rejections") to foreign bodies that must be treated with complex medication.

Depending on the placement of the implant device, various patient responses can be observed, ranging from "acceptance" of the foreign device by the human body, whereby the foreign material is passivated by fibrotic cell growth, to severe and uncontrollable inflammation and cell death. Regardless of the chemical reactions and biological transformations that take place around the implant, the human body's response to implants is usually to produce connective tissue sections, which interface with the implant's surface. However, in the long term, this reaction often leads to an excessive response (that is, an overgrowth of tissue sections) of the human body, called fibrosis. Endogenetic tissue damage is the first fibrotic stage and is caused by, for example, inflammation or circulatory disorder. These aspects are inherently present when implant devices are implanted in the patient as such devices are composed of foreign materials, which affect the blood circulation. To avoid inflammation after implantation, research efforts focus on the development of body-acceptable or bio-mimicking materials, chemical surface functionalization, for example, by providing inflammation-prohibiting additives, and chemical release of substances to control the patient's response upon implantation. In addition, in the long term, the blood circulation must be normalized again to prevent tissue damage.

While for many implants (including pacemakers), fibrotically passivated implant surfaces are the ideal final state (for example, after surgery) ensuring long-term usage, a novel class of implant devices are being developed, which aim at releasing chemical compounds (hormones, drugs, etc.) directly into the blood-supplied tissue and consequently into the blood circulation. There, a trade-off must be found between efficiently coupling the implant device via fibrotic responses to surrounding tissue (and then blood circulation) and an acceptable fibrotic passivation enabling long-term hosting of the implant. Furthermore, the delivery of compounds into the tissue can be an issue if it is only based on diffusion.

SUMMARY

According to a first aspect, the present invention is embodied as an implant device having a biointerface. The implant device comprises a cavity and a structure enabling a flow path between the cavity and the environment of the implant device. An actuatable membrane is interposed in the flow path. The device further includes a power-generating unit and a control unit, where the latter is connected to the power-generating unit. Moreover, an electromechanical system (for example, a microelectromechanical or a nanoelectromechanical system) is connected to both the control unit and the power-generating unit. The electromechanical system includes at least one actuator configured to mechanically contact the membrane. Preferably, this actuator is permanently attached to the membrane, for example, in a force-fit manner, on one side of the membrane. The control unit and the electromechanical system are jointly configured to cause the electromechanical system to controllably actuate the membrane via at least one actuator to control a transfer of substances between the cavity and the environment through the flow path.

Accordingly, the membrane can be actively and deterministically controlled, thanks to the electromechanical system, to regulate the extent to which substances can be transferred to/from the cavity of the implant device. Thus, the present approach makes it possible for the implanted device to manage exchanges of substances, to a desired level, between the implant device and its environment. This allows the delivery of substances into the environment of the implant device (for example, biological tissue) to be improved as passive diffusion is typically not sufficient to allow an efficient release of substances into the body, for example to reach physiologically relevant dose levels in metabolic processes.

In embodiments, the membrane is a deformable membrane. The control unit and the electromechanical system are jointly configured to cause the electromechanical system to controllably deform the membrane via at least one actuator and thereby control the transfer of the substances. The structure and the membrane may possibly be jointly configured to act as a unidirectional valve with respect to liquid in the cavity or the environment.

In embodiments, the control unit and the electromechanical system are jointly configured to cause the electromechanical system to actuate the membrane out-of-plane and accordingly to mechanically stimulate the environment of the implant device. This way, the device can efficiently tackle fibrosis.

Preferably, the electromechanical system comprises two or more actuators in mechanical contact with the membrane. The control unit and the electromechanical system are jointly configured to cause the electromechanical system to controllably deform the membrane, in-plane, via the two or more actuators, to control the transfer of the substances. More preferably, the two or more actuators include one or more pairs of actuators, each in direct contact with the membrane on one side thereof.

In particularly preferred embodiments, the actuators have, in each pair, a comb structure and are interdigitated. The electromechanical system can, for instance, be configured to electrostatically actuate the interdigitated actuators of each of the pairs to modify a distance between the interdigitated actuators.

In other embodiments, the electromechanical system further comprises elements interconnecting the actuators of each of the pairs. In that case, the electromechanical system is adapted to apply an electrical stimulus to said elements to cause a distance change between the interdigitated actuators by thermal expansion of these elements.

In embodiments where the membrane is configured to allow the substances to pass through it upon a deformation thereof, the membrane may, for instance, include a polymer. Preferably, the membrane is an ion-selective membrane having a surface coating designed to carry a static electric charge.

In preferred embodiments, the implant device further includes a support structure, and the membrane is fixed at one or more locations of the support structure. Preferably, the membrane is fixed to the support structure at one or more edges thereof. The implant device further includes auxiliary structures fixed to the membrane, and the actuators of the electromechanical system are anchored to the auxiliary structures.

In particularly preferred embodiments, the cavity comprises a bioactive material, which, for example, comprises cells. In that case, the cavity (or a chamber in this cavity) may be connected to the power-generating unit and configured to apply an electrical stimulus to the cells, for example, to trigger a certain process or reaction, prior to releasing an outcome of this process or reaction to the environment of the implant device.

According to another aspect, the invention is embodied as a method of operating an implant device. The method comprises providing an implant device such as described above, implanting the implant device in a biological environment, and operating the electromechanical system via the control unit. The electromechanical system is operated to controllably actuate the membrane via at least one actuator, with a view to controlling a transfer of substances between the cavity and the biological environment through the flow path. The electromechanical system may notably be operated to controllably actuate the membrane out-of-plane and accordingly mechanically stimulate the biological environment to prevent fibrosis.

In embodiments, the cavity comprises a given substance and the electromechanical system is operated to allow the given substance to migrate from the cavity to the biological environment through the flow path.

In more sophisticated scenarios, the cavity of the implant device provided comprises a bioactive material and the electromechanical system is repeatedly operated to first allow external substances to migrate from the biological environment to the cavity, for the external substances to react with the bioactive material in the cavity and yield a reaction product, and then allow the reaction product to migrate from the cavity to the biological environment.

According to a final aspect, the invention is embodied as a method of fabricating an implant device such as described above. The method first comprises providing a body of the implant device, where the body includes a cavity and a structure enabling a flow path between the cavity and the environment of the implant device. Then, an actuatable membrane is interposed in the flow path and an electromechanical system is obtained, which includes at least one actuator configured to mechanically contact the membrane. Moreover, a power-generating unit and a control unit are set, in or on the body. The power-generating unit is connected to each of the control unit and the electromechanical system, and the control unit is connected to the electromechanical system. This is done in such a manner that the control unit and the electromechanical system are jointly configured to cause the electromechanical system to controllably actuate the membrane via at least one actuator to control a transfer of substances between the cavity and the environment through the flow path.

In preferred embodiments, the electromechanical system is obtained by notably processing elements of the electromechanical system, these elements including at least one actuator, so as for the latter to be in contact with the membrane.

The elements of the electromechanical system typically comprise a plurality of actuators, each in direct contact with the membrane. The processing of the elements of the electromechanical system is preferably performed as follows. First, a layered silicon—insulator—silicon substrate is provided. The substrate comprises a silicon handle wafer, an oxide layer on top of the silicon handle wafer, and a topmost silicon layer on top of the oxide layer. The topmost silicon layer is patterned to obtain actuators (these including the at least one actuator) and the silicon handle wafer is etched using a deep reactive-ion etching process to define, in the silicon handle wafer, an empty space, which is at least partly delimited by lateral posts that are integral with respective ones of the actuators. Then, a part of the oxide layer is removed; this part is vis-à-vis the empty space. Finally, the posts are anchored to the membrane, on one side thereof, or possibly on two sides of the membrane.

Note, in the above embodiments of any of the aspects of the invention, the power and control units can optionally be separated from the implant itself (that is, the part of the device meant to be implanted), while remaining wired to the electromechanical system. In this case, the device comprises at least two parts, including, on the one hand, the implant (which comprises the cavity, flow path structure, membrane, and electromechanical system) and, on the other hand, the power and control units, where such parts are appropriately connected by one or more wires.

BRIEF DESCRIPTION OF THE DRAWINGS

These and other objects, features and advantages of the present invention will become apparent from the following detailed description of illustrative embodiments thereof, which is to be read in connection with the accompanying drawings. The illustrations are for clarity in facilitating one skilled in the art in understanding the invention in conjunction with the detailed description. In the drawings:

FIGS. 1A and 1B show 2D (two dimensional) cross-sectional views of an implant device according to embodiments, where the device includes a membrane that is actuated to control a transfer of substances between the device and its environment. FIG. 1B further shows electromechanical system elements actuating the membrane to deform it in-plane and allow substances to migrate from a cavity in the implant device to its environment, as in preferred embodiments;

FIGS. 2A-2B show simplified views of selected components of implant devices according to embodiments. FIGS. 2C and 2D are top views of pairs of electromechanical system actuators, according to embodiments.

In FIGS. 5A-5F, the membrane is deformed both in-plane and out-of-plane. In FIGS. 5G-5I, the membrane is merely translated out-of-plane;

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

Implant devices, methods of operation of such devices, and fabrication methods of such devices, will now be described, by way of non-limiting examples.

DETAILED DESCRIPTION OF EMBODIMENTS OF THE INVENTION

The following description is structured as follows. General embodiments and high-level variants are described in section 1. Section 2 addresses particularly preferred embodiments. All references Sn refer to methods steps of the flowchart of FIG. 7, while numeral references pertain to physical parts or components of the devices shown in FIGS. 1-6.

1. General Embodiments and High-Level Variants

Figure 1A:
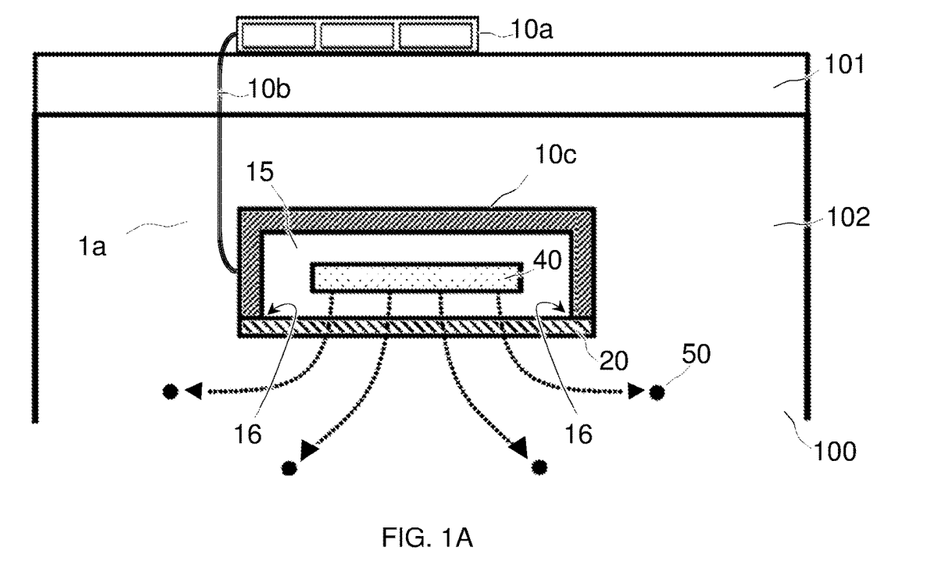
FIG. 1A shows a two-part implant device, including an implant part, which is implanted in a biological environment (here under the skin of a patient), while remaining wired to the control and power units arranged in a patch placed on the skin of the patient.
Figure 1B:
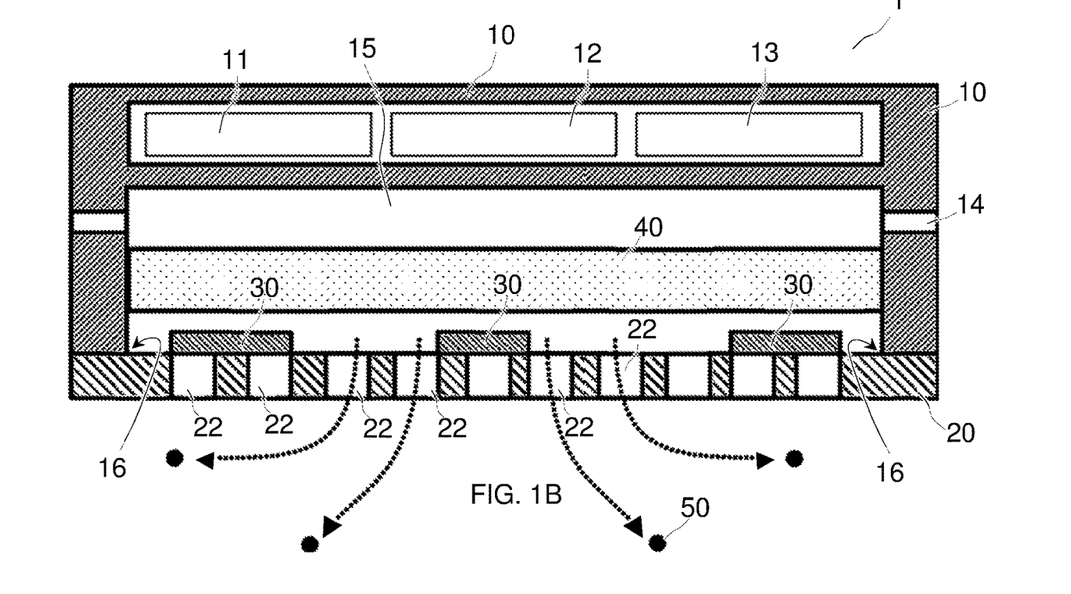
FIG. 1B illustrates another embodiment of the implant device, where the electromechanical system, the control and power units are all arranged in a same part, meant to be implanted.

In reference to FIGS. 1 and 2, an aspect of the invention is first described, which concerns implant device 1, 1a.

Implant device 1, 1a comprises cavity 15, which may notably include chamber 40, for reasons that will become apparent later. Device 1, 1a further includes structure 16 enabling a flow path between cavity 15 and environment 102 of implant device 1, 1a. This structure may be a mere aperture of cavity 15, for example, rim 16 (or a sealing ring) of the cavity, as assumed in FIGS. 1A and 1B. In variants, this structure may define one or more conduits or channels (or any other structural element defining a flow path) extending from the cavity to outside 102 of implant device 1, 1a.

Device 1, 1a further includes actuatable membrane 20, which is interposed in the flow path, so as to alter potential exchanges between the cavity and environment 102 of the device. Various configurations of the membrane can be contemplated, as described below in detail. The membrane may possibly form, together with one more surrounding structural elements, a valve, for example, a unidirectional valve.

Device 1, 1a also includes power-generating unit 11. Power-generating unit 11 may be an electrical unit, an electrochemical unit, or an electromechanical unit. It may also include piezo elements or other types of transducers, for example, photovoltaic or photochemical elements, for energy harvesting purposes.

Furthermore, device 1, 1a includes control unit 12, 13, which are connected to power-generating unit 11. The control unit may be any suitable electronic control unit (ECU), also known as electronic control module (ECM), for example, including a microcontroller supplemented by a static random-access memory (SRAM), an electrically erasable programmable read-only memory (EEPROM), and/or a Flash memory. The control unit may for instance be implemented as a system on a chip. If necessary, several control units 12, 13 may be provided, including, for example, master unit 12, as well as one or more auxiliary units 13, for example, one for controlling the membrane and one for stimulating substances in the chamber 40, if necessary. In addition to control functions, control unit(s) 12, 13 may also provide communication capability (for example, via wireless radio control) between the implant device and peripheral devices outside the body. FIG. 1B assumes a two-component control unit 12, 13, which includes main chip 12 for signaling and control purposes, and auxiliary chip 13 enabling communication capability.

Finally, device 1, 1a includes electromechanical system (EMS) 30, which is connected to both control unit 12, 13 and power-generating unit 11. EMS 30 includes at least one actuator, which is configured to mechanically contact membrane 20. In the following, the EMS is assumed to include two or more actuators 31, 32, which are typically arranged in pairs. Such actuators may permanently contact membrane 20 (for example, being attached to it) or intermittently contact the membrane, upon actuation thereof.

Importantly, control unit 12, 13 and EMS 30 are jointly configured to cause EMS 30 to controllably actuate membrane 20 via actuators 31, 32, in operation. This makes it possible for the device to control a transfer of substances 50 through the flow path. Depending on the application, the substances may possibly be transferred from cavity 15 to environment 102, from environment 102 to cavity 15, or successively from environment 102 to cavity 15 and then from cavity 15 to environment 102.

Device 1, 1a has a biointerface. The biointerface is the region of contact between the implanted part of implant device 1, 1a and its target environment 102, which may for instance be a human body or an animal body. In the following, the part 1, 10c of the device that is meant to be implanted is referred to as the "implant". In operation, when the implant is implanted in a human body or an animal body, biological environment 102 typically includes biological tissues, organs, etc. In addition, the implant may have to be placed in other biological environments, for example, in vitro environments, for development, experimental, or testing purposes. An in vitro environment essentially consists of a biological medium (including, for example, microorganisms, cells, or biological molecules, or other living organisms) which may be useful for development, experimental, and testing purposes, as in embodiments contemplated herein.

The biointerface will typically include all outer surfaces (for example, the outer shell) of the implant. It may notably include membrane 20, should the latter be exposed to target environment 102 of the implant, as in typical embodiments. The biointerface must be biocompatible, by definition. That is, the interface between the implant device and the surrounding medium must be made of biocompatible materials. Internally, however, implant device 1, 1a may include non-biocompatible materials such as metals, semiconductor, plastic materials, polymers, and oxides.

Cavity 15 may possibly include a bioactive material, as in preferred embodiments. The bioactive material may notably include chemicals or cells, which will produce chemicals, or any substance having a biological effect once the implant part is implanted and operated in its target environment 102.

Membrane 20 is interposed in the flow path, which impacts mass-flow exchange between cavity 15 and environment 102. This membrane can be suitably actuated to control exchange of substances 50 between the cavity and the environment, thanks to EMS 30, which is controlled by control unit 12, 13 and powered by power-generating unit 11. For example, the membrane can be arranged in body 10, 10c of implant device 1, 1a to close access to the cavity or, at least, restrict exchange of substances 50 between the cavity and environment 102 when membrane 20 is in a resting (or neutral) state.

For instance, the membrane may cap aperture 16 of cavity 15, or a channel, a conduit, or another structural element leading to the cavity. However, membrane 15 will not necessarily prevent access to the cavity, even if it caps the latter. For example, membrane 20 may be designed to allow diffusion-driven mass-flow exchange of substances. For example, when using a semipermeable membrane 20, it is still possible, even if the membrane is apparently closing the cavity, to transfer certain types of particles or substances between the cavity and environment 102, in one direction or the other, or in both directions, this depending on the actual design of the membrane itself and the intended application. Still, in preferred embodiments, the membrane typically closes (or partly closes) access to the cavity in its neutral state, as assumed in FIGS. 1A, 1B, as well as in FIGS. 5A-5F and 5H.

Figure 5A:
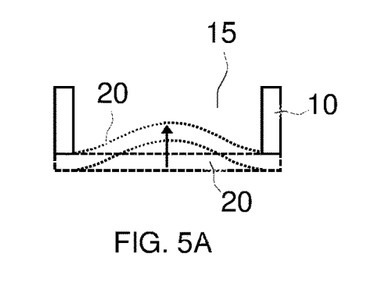
FIGS. 5A-5I are simplified cross-sectional views illustrating various possible ways of actuating membranes of implant devices according to embodiments.
Figure 5B:
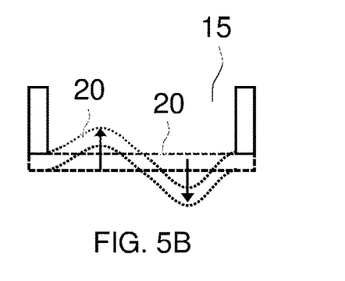
Figure 5C:
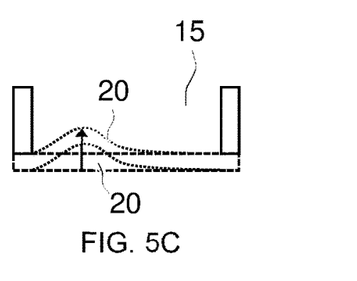
Figure 5D:
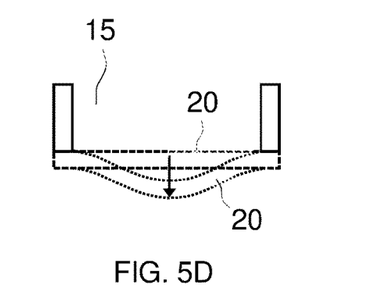
Figure 5E:
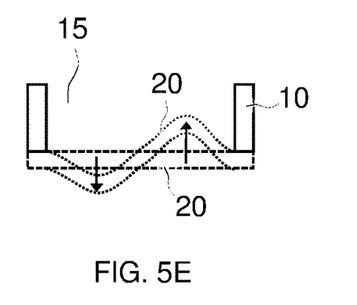
Figure 5F:
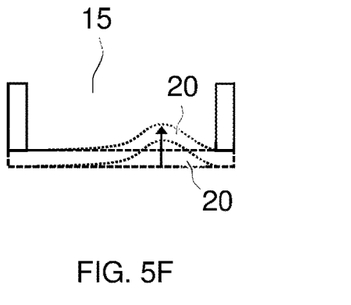
Figure 5G:
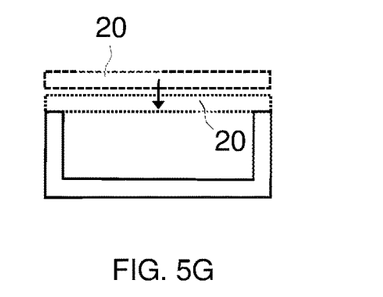
Figure 5H:
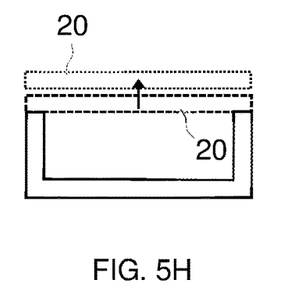
Figure 5I:
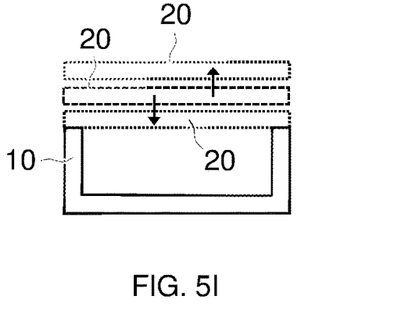

In variants, the neutral state of the membrane forms an open configuration (as in FIG. 5G), allowing particles or substances to move between cavity 15 and environment 102 of the implant. In that case, the membrane may be actuated to close the cavity or, at least, restrict access to it, as in FIG. 5G. Conversely, the membrane may also be actuated to increase potential exchange (for example, of fluids) between cavity 15 and environment 102, as illustrated in FIG. 5I Note, in FIGS. 5A-5I, the neutral state of membrane 20 is represented by dashed lines, whereas dotted lines depict an actuated (that is, deformed or translated) state of the membrane. As one understands, the membrane may, together with a surrounding structure, form a valve, which is operated so as to impact exchange of the substances with environment 102 of the implant.

Membrane 20 can, in fact, be actuated by moving it and/or deforming it, as illustrated in FIGS. 1B, and 5A-5I When actuated, membrane 20 causes to modify (that is, increase or decrease) the extent to which substances 50 can be transferred between cavity 15 and environment 102. For example, the membrane can be deformed in-plane only (as assumed in FIG. 1B), out-of-plane only (as assumed in FIGS. 5G-5I), or both in-plane and out-of-plane, as illustrated in FIGS. 5A-5F. In particular, the membrane may be actuated so as to create an under pressure (respectively an over pressure) inside the cavity, leading to an increased exchange of substances to (respectively from) cavity 15. In all cases, membrane 20 can be actively and deterministically controlled, thanks to EMS 30, to regulate the extent to which substances can be exchanged to/from cavity 15. Thus, the present implant devices 1 make it possible to let the implanted device automatically manage exchange of substances between the device and its environment. Once suitably programmed to do so, the device 1, 1a will typically be autonomous. In variants, device 1, 1a may be remote-controlled, provided it is equipped with a suitable receiver (for example, in the patch 10a, as assumed in FIG. 1A). In further variants, the implant device may form a close-loop system in combination with feedback received from other devices, for example, sensing elements.

Membrane 20 is not necessarily permeable (especially when it is actuated out-of-plane to open/close exchanges of substances between cavity 15 and environment 102), although it can be. The membrane may, for example, include a polymer material and/or be micro-structured, for example, include micro-pores 22. The micro-pores are preferably actuated by strain, whereby in-plane constraints are applied to the membrane, which leads to opening or closing the pores, as assumed in FIGS. 1B, and 2-4. The membrane may thus have various degrees of permeability, for example, be permeable, semi-permeable, or non-permeable to certain types of particles or substances. It may also be selective to certain chemicals (for example, permeable to certain ions or nutritive components) and be designed as a unidirectional, permeable membrane, as known per se.

In embodiments involving a (partly) permeable membrane, substances 50 may already pass through the membrane, even when the latter is in a resting (or neutral) state. Yet, deforming the membrane in-plane (as illustrated in FIG. 1B) modifies the extent to which such substances can pass through the membrane. In variants, the membrane is designed to cooperate with a channel, or some structural element defining a flow path that the membrane closes in its resting state. Once actuated or deformed, the membrane reaches a further state, which allows substances 50 to pass via this channel or path, as illustrated in FIG. 5G-5I.

In all cases, the actuation of the membrane by EMS 30 modifies the permeability of the membrane, or more generally, somehow alter its capacity to filter or transmit substances to and/or from the cavity. Importantly, the actuation of membrane 20 may further cause to stimulate surrounding tissues, thereby increasing blood circulation in such tissues, for example, to control and/or prevent fibrosis, as in embodiments contemplated herein.

Control unit 12, 13 ensures basic operations. It is powered by power-generating unit 11, which further powers EMS 30. The power-generating unit may further be used to apply an electrical signal to substances in the cavity, such as cells or chemicals, if necessary. That is, use can be made of electrochemical triggers, as in embodiments discussed later.

EMS 30 is typically designed as a micro- or nano-EMS, that is, a MEMS (microelectromechanical system) or a NEMS (nanoelectromechanical system). EMS 30 includes one or more actuators 31, 32. Note, power elements 11 and control elements 12, 13 may possibly be regarded as forming part of the EMS. However, for the purpose of the present description, power and control elements 11-13 are considered as distinct elements. In any manner, the EMS is used to control the actuation (for example deformation and/or translation) of the membrane, via the actuators, to regulate exchanges of substances between the cavity and the environment of the implant.

EMS 30 is controlled by control unit 12, 13 to allow membrane 20 to be controllably actuated, via actuators 31, 32. These actuators are designed to be or come in mechanical (or direct) contact with the membrane. That is, the actuators do not necessarily need to remain in mechanical contact with the membrane throughout the entire actuation trajectory. Rather, the actuators may, upon actuation, possibly come in mechanical or direct contact with the membrane or get out of mechanical or direct contact with the membrane, so as to cause to actuate the membrane, and accordingly impact the transfer of substances 50 to/from cavity 15. Thus, the actuators of EMS 30 may only intermittently contact membrane 20, for example, on one side thereof or on opposite sides of the membrane, to mechanically actuate the latter. Preferably though, the actuators are permanently fixed to the membrane, as assumed in FIGS. 1-4. Having actuators that are permanently fixed to membrane 20 allow a simpler and more robust design.

In the embodiments illustrated in FIGS. 1-4, membrane 20 is actuated so as to be deformed in-plane, which results in, for example, opening pores 22 or other microstructures of membrane 20. This can notably be achieved through actuators 31, 32 that consists of pairs of functionally related elements, for example, interdigitated, comb-like structural elements, as shown in FIG. 2C. Such elements are electrostatically actuated. Pairs of actuators may also be actuated by thermal expansion of some interconnecting elements 35, as shown in FIG. 2D. The actuators may include posts, which may be force-fit into membrane 20, glued to it, or attached to the membrane via auxiliary structures 27.

All this is now described in detail, in reference to particular embodiments of the invention. To start with, membrane 20 may be a deformable membrane, as assumed in FIG. 1B. Operating EMS 30 causes to controllably deform membrane 20 via the actuators (not shown in FIG. 1A or 1B) of the EMS and thereby control the exchange of substances 50. Note, the deformation of the membrane is assumed to be in-plane only in FIG. 1B. Here, the in-plane deformation causes to open pores of membrane 20, which increases the propensity of the membrane to let particles 50 pass through it. The examples shown in FIGS. 1A and 1B assumes that membrane 20 is actuated to allow substances 50 to migrate from cavity 15 to environment 102. In variants, or in addition, the membrane may be actuated to allow external substances to enter cavity 15 and interact (or react) with internal substances or processes. The product of this interaction or reaction can then be released in target environment 102, as in embodiments discussed later.

In variants to in-plane deformations, the membrane may be deformed and/or translated out-of-plane, to achieve a similar result. In other variants, membrane 20 can be deformed and/or translated both in-plane and out-of-plane. While an in-plane deformation typically causes membrane 20 to be more permeable, an out-of-plane actuation may further cause to stimulate environment 102, mechanically. That is, EMS 30 may be used to actuate membrane 20 out-of-plane and accordingly stimulate environment 102 mechanically, for example, to prevent fibrosis. In that case, not only substances 50 can be delivered to/from cavity 15 but, in addition, the actuation of membrane 20 causes to mechanically stimulate external tissues. For instance, implant device 1, 1a may be designed to produce bioactive substances that are released through the membrane, while surrounding tissue is stimulated by mechanical forces to promote the uptake of this bioactive substances and prevent thereby fibrotic tissue transformation.

As illustrated in FIG. 1A, device 1a may include two parts 10a, 10c, including external patch 10a, which includes power and control units 11-13, and implant 10c itself, meant to be implanted in the biological environment, for example, under the skin of the patient in the example of FIG. 1A. Implant 10c remains wired to external patch 10a, which can for instance be placed on the skin of the patient; wire connection 10b ensures power supply to the power-actuated EMS elements and, if necessary, signaling for control. In variants such as depicted in FIG. 1B, EMS 30, and control and power units 11-13 are all arranged in the same part 10, meant to be implanted. The following description mostly assumes a single-part device 1, in which components 11-13 and 30 are all arranged in a same part, as depicted in FIG. 1B.

Figure 2A:
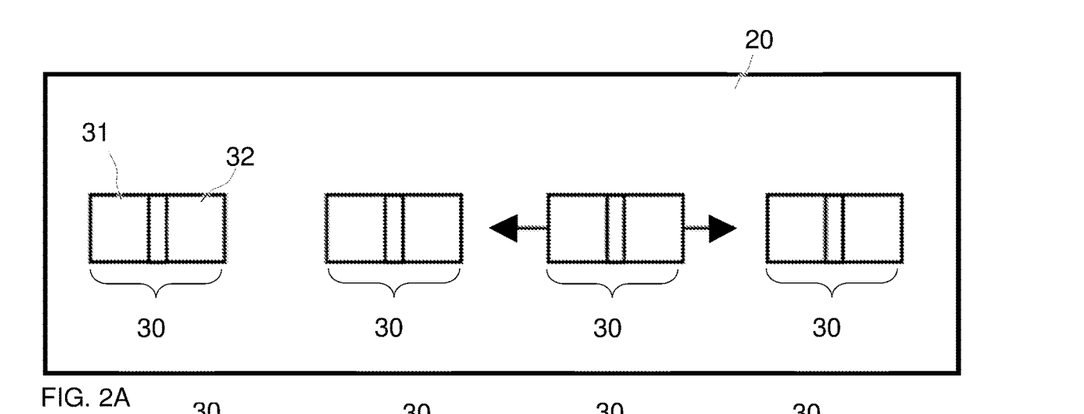
FIG. 2A is a top view of a membrane; onto which pairs of electromechanical system actuators are attached in a force-fit manner.
Figure 2B:
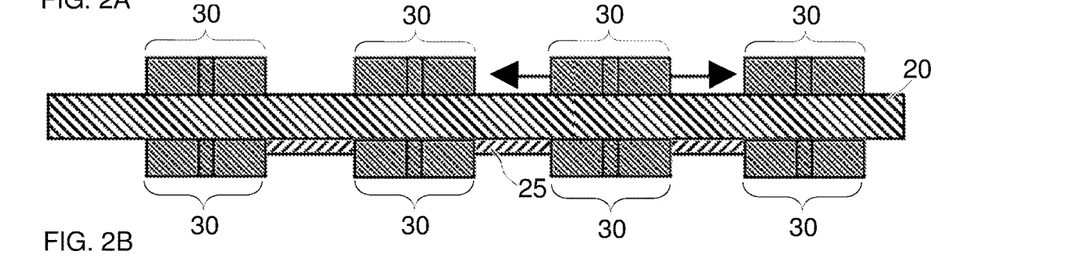
FIG. 2B is the corresponding cross-sectional view.
Figure 2C:
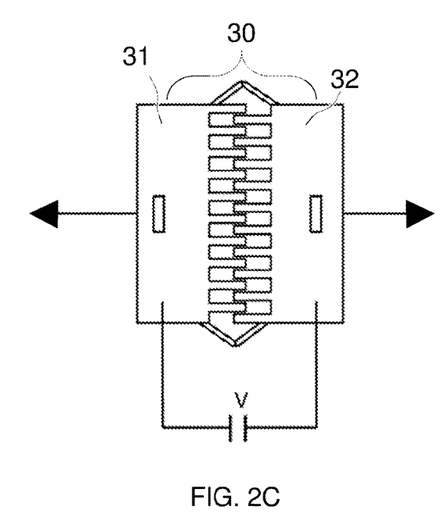
FIG. 2C shows comb-like, interdigitated actuators that are electrostatically actuated, whereas the actuators of FIG. 2D are actuated by thermal expansion of interconnecting elements.
Figure 2D:
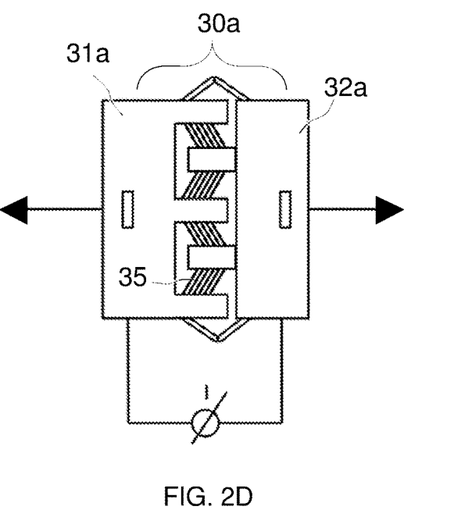
Figure 3A:
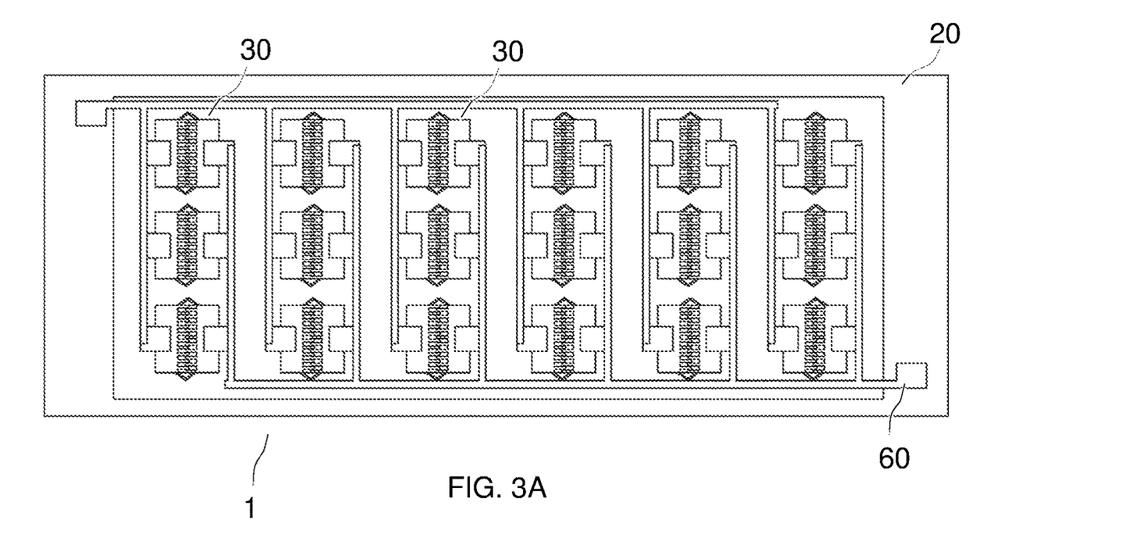
FIGS. 3A and 3B show a top view and a bottom view, respectively, of selected components of an implant device according to embodiments, in which multiple pairs of electromechanical system elements are attached to a flexible membrane, as in embodiments.
Figure 3B:
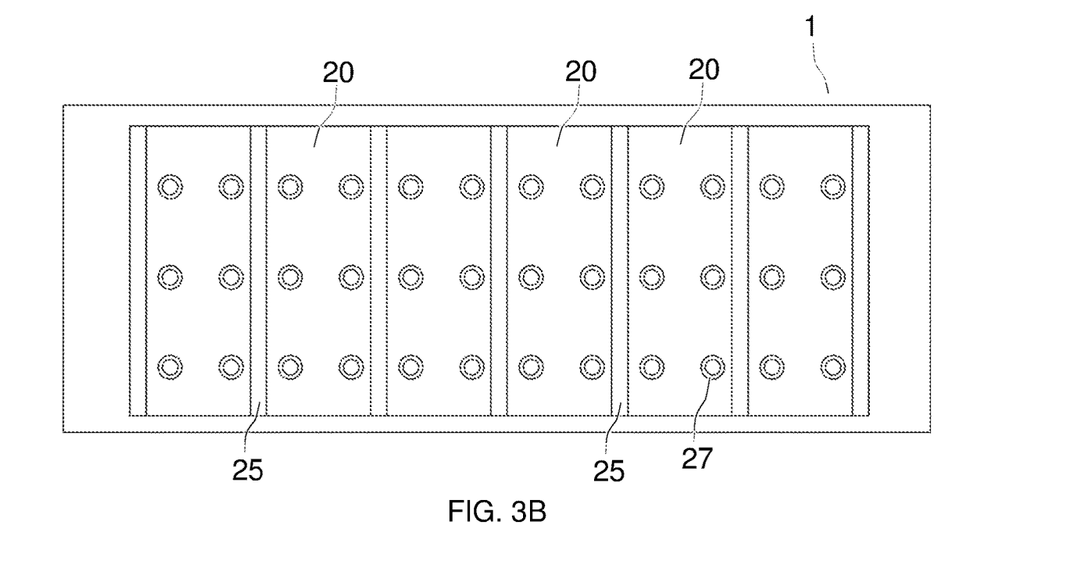
Figure 4A:
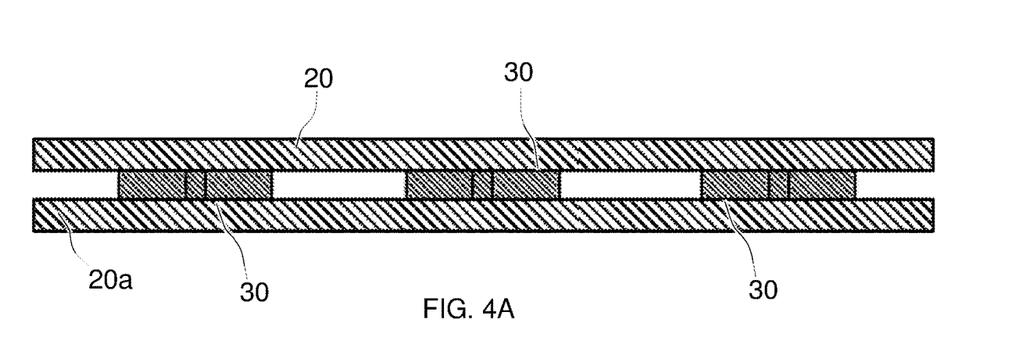
FIGS. 4A and 4B are 2D (two dimensional) cross-sectional views of selected components of an implant device involving two membranes, as in embodiments.
Figure 4B:
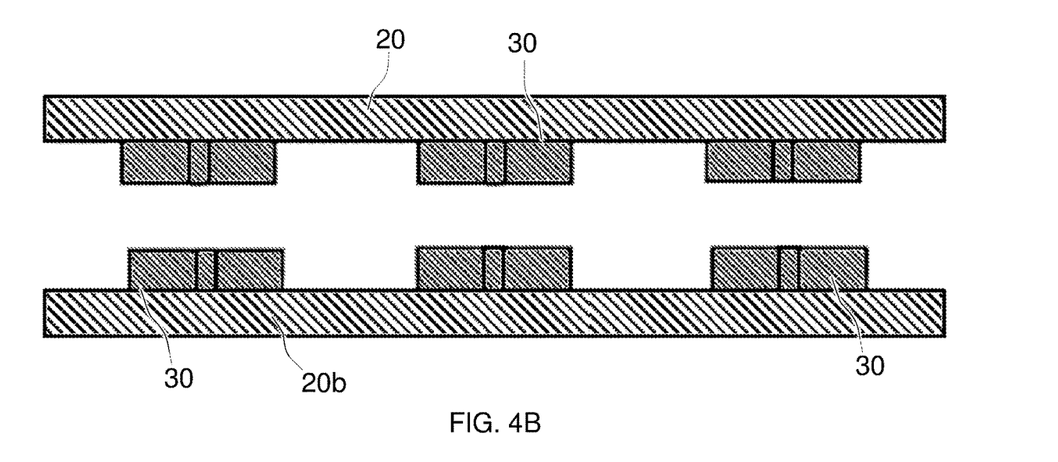

Preferred arrangements of EMS actuators are now described in reference to FIGS. 2-4. EMS 30 preferably comprises a plurality of actuators 31, 32, which are permanently fixed in mechanical contact with membrane 20. Such actuators are preferably arranged in pairs, as seen in FIGS. 2A, 2B, 2C, and 2D. Actuators of each pair may notably be arranged side-by-side, with a view to controllably deforming membrane 20, in-plane, via actuators 31, 32 (31a, 32a) of each pair, to control the transfer of the substances. Where the EMS actuators are designed to operate in-plane with respect to membrane 20, the relative distance between the actuators changes, which results in an in-plane deformation of membrane 20.

Actuators 31, 32, may for instance be, each, in direct contact with membrane 20, for example, on one side thereof (as in FIG. 3A or 4B), or on opposite sides of a same membrane, as in FIG. 2B. In variants, the actuators may be permanently attached to opposite sides of two membranes 20, 20a, in vis-à-vis. The pairs of actuators may also be arranged all in a same plane, between two opposite membranes 20, 20a, as in FIG. 4A. Each actuator is attached to each membrane in that case. In variants, distinct sets of pairs of actuators may be arranged on each membrane 20, 20b, on the interior side thereof, as in FIG. 4B. In the embodiments illustrated in FIGS. 4A and 4B, the implant device involves two membranes, which contributes to define a cultivation chamber for compounds (for example, cells). The latter are electrically stimulated, for example, by pairs of electrodes providing electric fields or charge-carriers to interact with the compounds (not shown).

As evoked earlier, the actuators of the EMS may notably be actuated electrostatically and/or thermally, as now discussed in detail in reference to FIGS. 2B, 2C, and 3A. In the example of FIG. 2C, the pair of actuators 31, 32 have a comb structure and are interdigitated. EMS 30 may include several of such pairs, as shown in FIG. 3A. The EMS may be configured to electrostatically actuate interdigitated actuators 31, 32 of each pair, in order to controllably modify the distance between them. To that aim, each pair is connected to an electrical circuit, including a controllable voltage source, as symbolically shown in FIG. 2C. Note, in practice, the electrical circuit forms part of an electronic circuit including control unit 12, 13, which controls the voltage applied to actuators 31, 32. Preferably, a same voltage is applied, in parallel, to the actuators of each pair, such that a same local deformation is imposed throughout membrane 20. This is illustrated in FIG. 3A, where a 2D (two dimensional) arrangement of pairs 30 of actuators are connected through electrical connectors 60 or traces, themselves connected to control unit 12, 13 (not shown in FIG. 3A).

In variants, the EMS include pairs 30a of actuators 31a, 32a that are interconnected by elements 35, where such elements can be subjected to thermal expansion, see FIG. 2D. That is, the pairs of actuators are connected to an electrical circuit and EMS 30 is adapted to apply an electrical stimulus to elements 35, which causes to modify a distance between the actuators 31a, 32a, due to the thermal expansion of elements 35. Such elements 35 preferably have an aspect ratio. That is, they can typically be designed as thin, elongated elements. The electrical stimulus applied may be a current (as assumed in FIG. 2D) or a voltage bias. Elements 35 may also be regarded as microheaters, operating based on Joules heating. However, it may be sufficient to rely on the spatial arrangement of undoped and doped semiconductor elements and apply a voltage bias or drive a current through the actuators, via elements 35, the low-doped region of which then heats up as desired as a result of the high electrical resistance the charge-carrier experience, the extent of the heating being essentially determined by the local doping and the electrical load applied.

In further variants (not shown), the actuators may be designed as a bilayer structure of two different materials, having different coefficients of thermal expansion. Each pair of actuators forms a bilayer structure, which is attached to one side of the membrane. For example, the EMS may be configured as a MEMS involving two pairs (each including two materials) affixed to the membrane at two positions thereof, for example, at two ends of the membrane. The thermal expansion differs in each layer, causing each of the pairs to bend. Thus, each pair forms a bending beam, which can be used to locally bend the membrane upwards or downwards. Several pairs may be arranged across the membrane to achieve deformations such as shown in FIGS. 5A-5F. Of course, the linear/uniaxial deformations shown are not to scale and may protrude to the dimension not shown, creating multi-axial deformations.

In other variants (not shown), the EMS may include coils, which do not physically contact the membrane but interact magnetically with elements (responsive to magnetic or electrical fields) affixed to the membrane to actuate or deform the latter.

Various types of membranes are now discussed in detail. As depicted in FIG. 1B, membrane 20 may notably be configured to allow substances 50 to pass through membrane 20 upon a deformation thereof, for example, an in-plane deformation in the example of FIG. 1B. Membrane 20 may notably be porous or, more generally, include one or more microstructures formed across the membrane. As illustrated in FIG. 1B, deforming the membrane in-plane causes the microstructures to change their size (for example, their average diameter across the membrane), which allows certain substances 50 to pass through the membrane.

Membrane 20 may notably include or consist of a polymer, such as polyvinylidene fluoride (PVDF) or polyethersulfone (PES). If the membrane happens to be exposed to environment 102 of device 1, then it should be made from a biocompatible material, as is the case with PVDF or PES. In embodiments, membrane 20 is an ion-selective membrane 20; it may notably have a surface coating carrying a static electric charge (that is, causing a change in the surface potential). Note, membrane 20 may already enable ion filtering, passively, but the deformation induced by the EMS will nevertheless impact the transfer of substances 50 through the membrane, either by changing the mass-flow exchange rate or act as ion-selective filter. Note, the membrane may also happen to be ion-selective just because of its porosity. In that case, deforming the membrane provokes changes in its morphology, for example, its pore sizes, which again impacts the transfer of substances 50.

As illustrated in FIG. 3B, implant device 1 may further include support structure 25, onto which membrane 20 is fixed, glued, or otherwise mechanically attached. The membrane is preferably fixed at several locations of support structure 25. Support structure 25 may for instance be a frame or a rim, or it may have a more sophisticated structure. In the example of FIG. 3B, support structure 25 includes a rectangular rim with transversal bridges, to which the membrane is attached. The membrane is further attached to the peripheral edges of the rim. This results in constraining membrane 20 and ensures a restoring mechanical force to the membrane, where this force typically works against the EMS actuation direction. More generally, support structure 25 may have any suitable shape, adapted to cavity 15, for example, contributing to enclose the cavity. Apparent rings 27 are anchors for actuators 31, 32 seen in FIG. 3A. More precisely, rings 27 are auxiliary structures 27 that are fixed to membrane 20 and actuators 31, 32 of EMS 30 are anchored to auxiliary structures 27.

In variants such as illustrated in FIGS. 2A, 2B, 4A, and 4B, actuators 31, 32 are attached to membrane 20 in a force-fit manner on one side of membrane 20 (FIGS. 2A, 2B) or on inner sides of opposite membranes (FIGS. 4A, 4B). That is, the actuators are forced pressed into a superficial thickness of membrane(s) 20. In all cases, the movement of EMS actuators 31, 32, 31a, 32a is transferred to the membrane, at least locally.

In the accompanying drawings, membranes 20, 20a are assumed to be essentially planar objects. However, various membrane designs can be contemplated. For example, a membrane may include deformable valve elements such as elastic flaps, similar to flaps seen in a venous valves. In other variants, membrane 20 may form, together with rim 16 and/or support structure 25, a unidirectional valve with respect to substances (for example, in a liquid matrix) in cavity 15 (for example, in chamber 40) or environment 102. More generally, membrane 20 may cooperate with one or more structural elements (forming flow paths or channels) to form valves, which allow substances 50 to be controllably exchanged to and/or from cavity 15. Such valves may be designed as unidirectional valves (in one or the other direction) with respect to liquid in the cavity or environment 102. Moreover, device 1 may include a variety of additional microstructures, such as valves or vents 14.

In preferred embodiments, cavity 15 comprises a bioactive material. This material may notably include cells. In that case, cavity 15 may advantageously be connected to power-generating unit 11, so as to be able to apply an electrical stimulus to the cells. For example, cavity 15 may comprise electrodes, as well as electrically conducting elements connecting the electrodes to allow an electrical stimulus to be applied to the cells. Again, the electrical stimulus can be an electrical voltage or current. This makes it possible to use electrochemical triggers, as in embodiments.

Referring to FIG. 6, a second aspect of the invention is now described, which concerns a method of fabricating an implant device such as described above.

The fabrication method first comprises providing a body of the implant device. The body includes cavity 15 and structure 16 enabling a flow path between cavity 15 and the environment of the implanted part of the device.

Then, membrane 20 is interposed (for example, attached to support structure 25) in the flow path and EMS 30 is obtained. The latter includes at least one actuator 31, 32, which is configured to mechanically contact membrane 20. Note, the EMS may possibly be obtained prior to fixing the membrane, as in embodiments described below.

Moreover, power-generating unit 11 and control unit 12, 13 can be set (that is, installed), in or on the body. The power and control units may possibly be installed prior to obtaining the EMS and/or fixing membrane 20. In variants, the power and control units are set in an external part 10a, as noted earlier in reference to FIG. 1A. Eventually, power-generating unit 11 is connected to each of the control units 12, 13 and EMS 30 and control unit 12, 13 is connected to EMS 30. Consistently with the first aspect of the invention, the implant device is fabricated in such a manner that control unit 12, 13 and EMS 30 are jointly configured to cause EMS 30 to controllably actuate membrane 20 via actuator(s) 31, 32, so as to be able to control the transfer of substances 50 between cavity 15 and environment 102 through the flow path, in operation of the implant device.

The installations and connections of the power and control units are fairly straightforward. Similarly, membrane 20 can be fixed using techniques well known in the art, for example, in microfluidics, including gluing, bonding, screwing. An example of a suitable technique has been described in reference to FIG. 3B. An important step of the fabrication consists in obtaining a suitable EMS 30 and connecting it, mechanically, to the membrane.

The EMS can be fabricated using known MEMS- or NEMS fabrication techniques. Most simple is to fabricate EMS 30 by processing elements thereof (including the actuators), so as for the actuators to be in direct or mechanical contact with membrane 20. That is, the actuators are permanently attached to the membrane in that case, for example, force-fit into the membrane, as assumed in FIGS. 2-3.

The elements of EMS 30 may advantageously be processed as illustrated in FIGS. 6A-6H. One starts with a layered silicon—insulator—silicon substrate 81-83, see FIG. 6A. The substrate comprises silicon handle wafer 81, oxide layer 82 on top of silicon handle wafer 81, and silicon layer 83 on top of oxide layer 82, referred to as topmost silicon layer in this document and also known as device layer in the literature. The oxide layer is also referred to as buried oxide (BOX) in literature and mostly consists of silicon oxide ($SiO_2$). That is, the initial substrate may be a silicon-on-insulator (SOI) substrate.

Figure 6A:
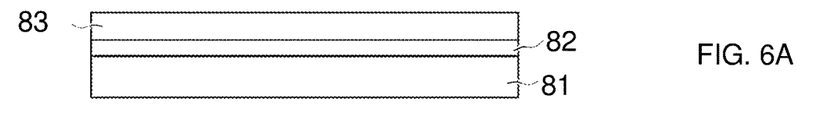
FIGS. 6A-6H are 2D (two dimensional) cross-sectional views illustrating the fabrication of elements of an electromechanical system and their fixation to a membrane of an implant device, according to embodiments.
Figure 6B:
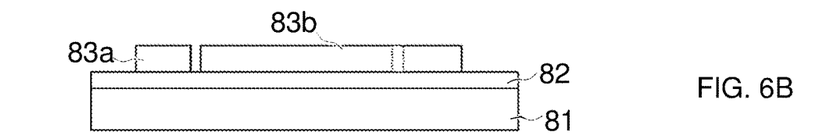
Figure 6C:
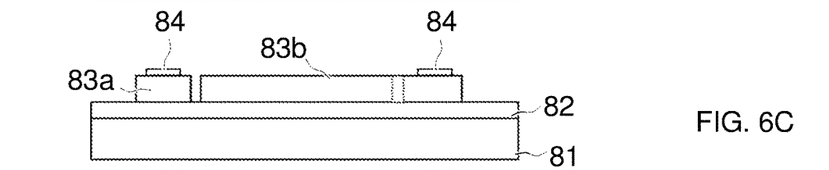
Figure 6D:
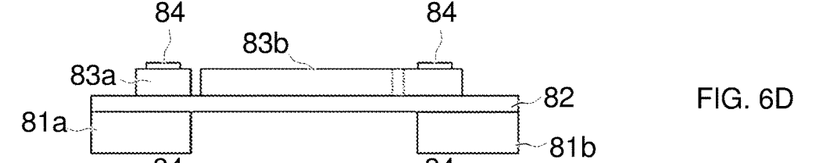
Figure 6E:
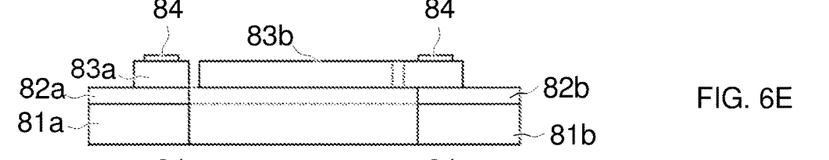
Figure 6F:
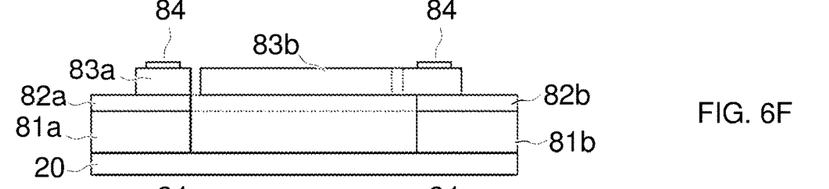
Figure 6G:
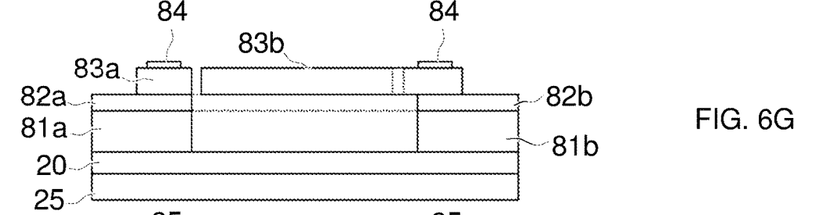
Figure 6H:
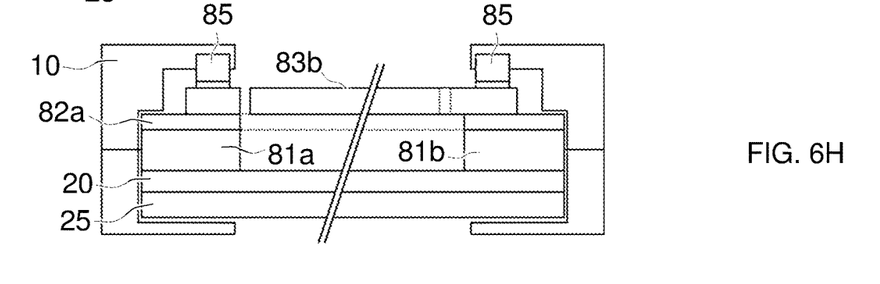

As seen in FIG. 6B, topmost silicon layer 83 is patterned to obtain parts 83a, 83b of actuators using, for example, deep reactive etching (DRIE). Note, FIGS. 6A-6H are cross-sectional views. The actuator members are assumed to be interdigitated in this example, hence the dash lines in FIG. 6B, which represent the next row of electrodes interrupted to the other side. Next, one may lithographically structure metal pads 84 on top of the actuators, as depicted in FIG. 6C. If necessary, a planarization step for conformal spin-coating of resists may be performed and the native-oxide removed prior to depositing the metal contact (not shown). Note, the metal pads may possibly be deposited at another point in time. Next, silicon handle wafer 81 is partially etched using DRIE to define an empty space in silicon handle wafer 81. The DRIE process stops selectively on the BOX layer. As seen in FIG. 6D, this empty space is at least partly delimited by lateral posts 81a, 81b, which are integral with respective ones of the actuator parts 83a, 83b. The handle waver is preferably etched using a combination of photolithography and DRIE. The part of oxide layer 82 that is vis-à-vis the empty space is subsequently removed, while residual lateral portions 82a, 82b of the oxide layer 82 remain, see FIG. 6E. For example, the BOX layer can be selectively removed by a buffered HF dip/wet etching. If necessary, additional steps may be involved, for example, to mask the metal pads. After that, posts 81a, 81b are anchored to membrane 20, on one side thereof, as seen in FIG. 6F. If necessary, this process may be mirrored on both sides of membrane 20, to achieve a device as shown in FIG. 2B. In variants, this process is repeated in respect of a further membrane, to fabricate a device as shown in FIG. 4B. Assuming that the membrane is a polymeric membrane, one may notably glue the posts, or use laser welding or a photocurable resist to attach the posts to the membrane. In variants, the posts are force-fit into the membrane, as evoked earlier. The structure can finally be reinforced by metal support 25 (FIG. 6G) and mounted to implant body 10 (or housing), FIG. 6H. Then, control and power units are connected to the interdigitated electrodes, for example, by bonding when such units are meant to be set in the same body 10 as EMS 30. The implant can then be implanted in body 10. Electrical contact is typically achieved through electrodes 85 set on top of the metal pads 84, see FIG. 6H. In variants where the control and power units remain outside the body, the EMS elements are further connected through wires to external patch 10a.

As noted earlier, EMS 30 may possibly be fabricated as a microelectromechanical system (MEMS) or a nanoelectromechanical system (NEMS). When designed as an NEMS, EMS 30 includes at least one element having a characteristic dimension between 1 and 100 nanometers. When designed as a MEMS, the smallest element of EMS 30 has a characteristic dimension that is between 100 nanometers and 100 micrometers. That said, the EMS may possibly include both nanoscale elements and microscale elements. The EMS preferably includes a plurality of elements, including, for example, a plurality of pairs 30, 30a of actuators, as assumed in FIGS. 2-4. Beyond the preferred fabrication methods discussed above, additional fabrication methods of MEMS and NEMS are known, which may possibly be used in the present context.

Figure 7:
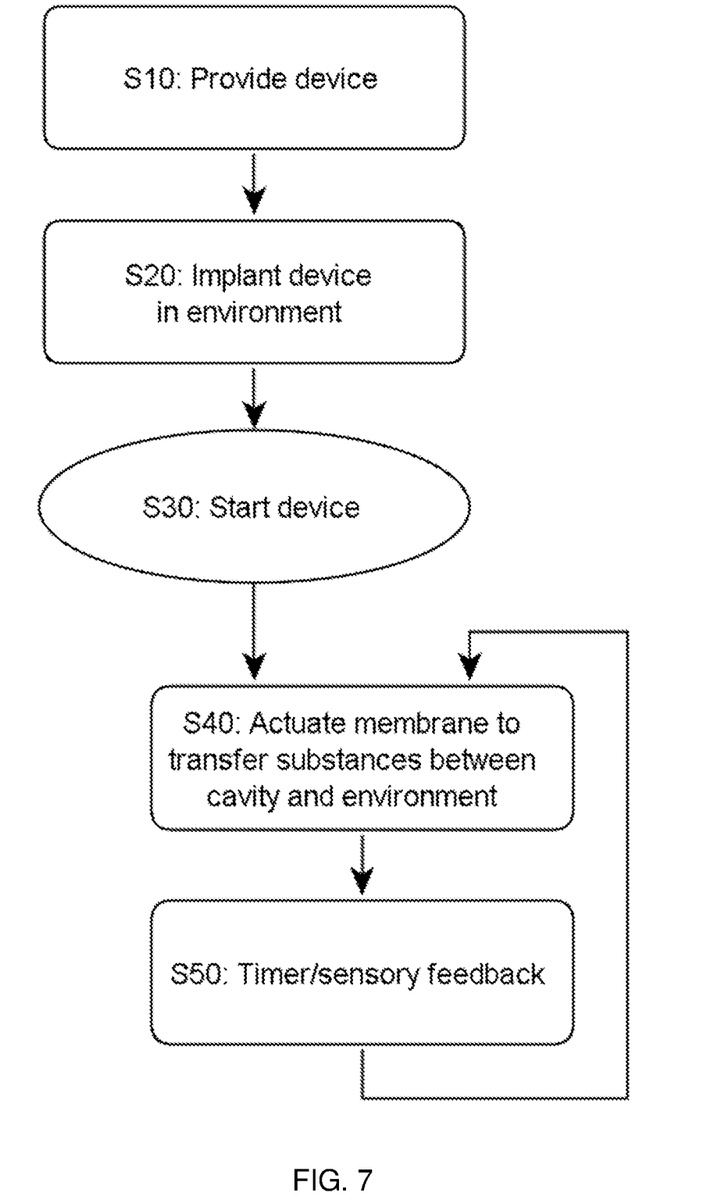
FIG. 7 is a flowchart illustrating high-level steps of a method of operating an implant device according to embodiments.

Referring to FIG. 7, a final aspect of the invention is now described, which concerns a method of operating an implant device such as described above. Essential aspects of this method have already been described in reference to the first aspect of the invention. Accordingly, this method is only briefly described in the following.

Clearly, the implant part of the device is meant to be implanted in the body of a patient. For instance, FIG. 1A illustrates device 1a, which includes implant 10c that is implanted in biological tissue 102, under the skin 101 of patient's body 100. More generally, however, the present implants may be implanted or placed in any biological environment for, for example, testing, development, and/or experimental purposes. This environment may be or include a biological medium that can be, for example, blood or tissue. The biological medium may further be a synthetic medium. The following describes a method, in which the implant is implanted in an in-vitro medium.

As seen in FIG. 7, an implant device is first provided at step S10. This implant part of the device is then implanted (step S20) in a biological environment. From this point on, the EMS can be operated S30-S50 via control unit 12, 13, to controllably actuate S40 membrane 20 via actuators 31, 32 of the EMS. This, in turn, makes it possible to control the transfer of substances 50 through the flow path in which the membrane is interposed. Substances 50 may notably be molecules or other particles acting as drugs, hormones, or neurotransmitters. Substances 50 may also be cells and other biological materials. As explained earlier, membrane 20 may notably be deformed (in-plane, out-of-plane, or both), translated, or otherwise moved by the EMS actuators. Of particular advantage is the possibility to actuate S40 membrane 20 out-of-plane to stimulate the biological environment mechanically, in addition to controlling the transfer of substances through the membrane, as discussed earlier.

In embodiments, cavity 15 comprises a given substance and EMS 30 is operated S30-S50 to allow this substance to migrate from cavity 15 to the biological environment 102, as illustrated in FIG. 1A. In other applications, however, more sophisticated exchanges are orchestrated via control unit 12, 13, for example, to allow the migration of reaction products from the cavity. In particular, cavity 15 of the implant may comprise a bioactive material. In that case, EMS 30 may be repeatedly operated S30-S50 to allow external substances to migrate, first from biological environment 102 to cavity 15, where they can react (or somehow interact) with the bioactive material in the cavity to yield a reaction (or interaction) product. Eventually, the reaction product can migrate from cavity 15 to biological environment 102.

Several interaction cycles may likewise be contemplated. This can be for instance achieved via a timer, in simple cases. For example, the cavity of the device may be loaded with a substance in a viscous matrix. After starting S30 the device (which may possibly be done remotely), the membrane is actuated S40 a first time, during a sufficiently long time to allow external substances to penetrate into cavity 15. Yet, the viscous matrix prevents the internal substance from escaping into the external environment. Once a first timer has elapsed S50, the actuation of the membrane is released S40 to close the cavity (or restrict access to it) and let the various reactants react. After a second timer has elapsed S50, the membrane is actuated S40 again to allow the reaction product to migrate to the environment. Such cycles can be repeated if needed. If necessary, the timer logic may use signals retrieved by other means, including measurements of metabolism, blood composition and levels of glucose, insulin, or other substances. Such signals may for instance enable a feedback-loop S50, which makes it possible to reach physiologically reasonable levels, for example, to cure diseases. So, a sensory feedback may be used in place of or in addition to the timer at step S50.

The above embodiments have been succinctly described in reference to the accompanying drawings and may accommodate a number of variants. Several combinations of the above features may be contemplated. Examples are given in the next section.

2. Specific Embodiments—Technical Implementation Details

This section describes particularly preferred embodiments of the implant device, which can notably be used to prevent, reduce, or tune, the fibrotic encapsulation at the interface between the implant device and host tissue, by using MEMS actuators. Namely, a polymeric membrane is actively and deterministically actuated via the MEMS. Beside controlling fibrotic encapsulation via the mechanical actuation of the membrane, cell oxygenation, nutrients, and drug exchanges, can be simultaneously enhanced. This makes it possible to better control the growth of fibrotic tissue and exchanges of chemicals through the membrane.

The following describes how MEMS can be used to: (i) prevent inflammation caused by circulatory disorder; and (ii) mass-flow couple the implant device to interfacial host tissue, whereby substances can be released thanks to an internal mechanism enabled by the MEMS. These tasks are achieved by mechanical actuation of the membrane to control diffusion and to provide pressure differences for mass-flow.

Preferred implant devices include: implant body 10 (a housing made from a biocompatible material); a polymeric, flexible membrane (made from a biocompatible material too); various MEMS components 30 including actuators 31, 32; and power and control units, which may be regarded as forming part of the MEMS. Optionally, the device may include fluid channels and form unidirectional valves, as evoked earlier. Examples of arrangements are depicted in FIGS. 1-3.

As seen in FIG. 1A, the implant 10c may notably be implanted subcutaneously, underneath skin 101 and inside host tissue 102, the primary goal being to deliver molecules such as mammalian hormones, drugs, etc. The device shown in FIG. 1B includes semipermeable membrane 20, cell cultivation chamber 40 for molecular stimulation or production, and MEMS components 30 attached to membrane 20.

In cultivation chamber 40, desired molecules are produced for subsequent delivery into the patient's body 100, see FIG. 1A. Possible mechanisms of molecular production may include opto-, mechano-, chemo-, or electrogenetic stimulation approaches of artificial designer cells (hosted permanently inside the cultivation chamber), biosynthetic methods, local drug repositories, etc. For electrogenetic stimulation, an electrical bias is applied to the cells by interdigitated electrodes (not shown) to electrogenetically produce hormones, for example, insulin. The electrodes in the cultivation chamber need to be electrically driven, an operation that requires battery 11, and microcontroller 12, 13, which are located inside housing 10. Methods for molecular factory operation may include magnetic fields and electrochemical methods.

The main part of housing 10 should remain passive with respect to mass-flow exchanges between cavity 15 (for example, cultivation chamber 40) and host tissue 102. Membrane 20 is the only interfacial structure that allows mass-flow exchange. Thus, the membrane needs to be permeable or semipermeable to allow small molecules, ions, etc., to pass through it while larger components (for example, cells) should be prevented to pass in this example. That is, the size-dependent filtering functionality of membrane 20 is important to control the process and exchanges in this example. Porous membranes may notably include a PTFE polymer or a biopolymer such as alginate. Yet, more sophisticated types of membranes may be contemplated, such as membrane include a micro-structured bearing inside a discrete liquid channel, filtering elements, etc. The membrane may further form, together with adjacent structural elements, a unidirectional valve, to enable a unidirectional mass-flow. Alternatively, cultivation chamber 40 (including electrodes) and the membrane can be physically combined into a single component.

The flexible membrane is actuated by mechanical forces. Mechanical operation is induced via MEMS actuators 31, 32 that are attached to the membrane, for example, in a force-fit manner on one or two sides of the membrane, as seen in FIGS. 2-4. Combined with the membrane's mechanical actuation, a unidirectional valve, if any, allows a directed delivery of substances 50.

As seen in FIGS. 2-4, the device preferably includes a plurality of pairs 30 of MEMS (or NEMS) actuators 31, 32 that are attached to flexible membrane 20, on one or two sides of membrane 20, for example, in a force-fit manner, such that the actuation of the MEMS actuators is transferred to the membrane, at least locally. The MEMS actuators can be designed to operate in an in-plane manner (with respect to the membrane). The direction of actuation of the MEMS actuators can be adapted to the desired mechanical actuation of the membrane. In simple implementations, the MEMS actuators may all have a same orientation, as seen in FIGS. 2A and 2B.

There exists a broad range of MEMS actuation principles for in-plane actuation. Most advantageous is to rely on comb structures (FIG. 2C) or microheaters (FIG. 2D). Comb structures involve interdigitated actuator parts 31, 32 (in fact electrodes), to which a driving voltage is applied. This results in an electrostatic force, which causes a relative displacement of actuator parts 31, 32. If necessary, additional cantilevered Moonie-type structures are used to act as motion enhancing or reducing elements, to constrain the motion to in-plane or out-of-plane or to add additional supports or structures to define a desired bending beam upon operation.

In variants, microheaters are used (FIG. 2D). That is, elements 35 of the MEMS are locally heated, which leads to a thermal expansion of elements 35. By design, a unidirectional motion can be enforced. Various methods are known to those skilled in the art, to cause local heating, for example current-driven Joule heaters with simple geometrical narrowing, or low electrical conductivity realized by local doping variations, etc. Due to the high thermal conductivity of materials such as silicon, the thermal cooling achieved by draining the excess heat induced towards the corpus of the device is fast, allowing the devices to operate at kHz frequencies, if necessary. In the present context, though, speed is not limiting as the membrane is preferably operated in the MHz to Hz frequency range. Similar to comb structures, Moonie/cantilever elements can be used to stabilize the device mechanically and to constrain the actuation of the actuator parts 31a, 32a to a 2D (two dimensional) plane.

In addition, the MEMS-membrane arrangement can be stabilized by one or two supporting layers 25, placed on one or two sides of membrane 20. Supporting layer 25 can be used to induce a passive mechanical, repulsive force to work against the unidirectional MEMS actuation or to increase the stability of the entire MEMS-membrane sandwich if a mechanically less rigid or highly porous membrane is used. Notably, the forces induced by MEMS 30 and counteracting support layer 25 can be tailored, for example, by locally structuring supporting layer 25.

Using a couple of MEMS actuators attached to the membrane, different mechanical modes can be induced to the membrane to control its bending profile. This is illustrated in FIGS. 5A-5I Note, the amplitudes are obviously not to scale, and the MEMS actuators are not shown for simplicity. The membrane actuation modes can be induced with MEMS actuators on one or two sides of the membrane, also in combination with supporting layer 25 that acts as a resetting structure, that is, a force-restoring element.

As discussed above, MEMS actuators can be used to deflect a flexible membrane of an implant device to create pressure differences and local diffusion in proximity of the membrane. In variants, the actuated membrane can also be used to stimulate cells inside cultivation chamber 40 by mechanical forces via hydrodynamic pressure differences. In combination with unidirectional valves, the membrane can act like a pump, owing to the pressure differences it can create. It can therefore be used to activate and control mass-flow. At the interface to the host tissue, the mechanical motion can be used to control active, well-blooded tissue growth and to maintain its physiological state. In variants, it can also be used to prevent fibrotic passivation of tissue as detrimental to mass-flow exchange and in particular to molecular drug delivery/hormone dosage.

Electrostatic actuators are well known in the field of MEMS and microfabrication technology. A variety of example of MEMS devices are known, which have different shapes and structures depending on the targeted application. The fabrication process required may also be adapted, depending on the substrate used. In the present context, it is preferred to make use of a standard electrostatic MEMS actuator fabricated from a SOI substrate, as discussed in the previous section.

Given the range of possible functionalities that can be realized by MEMS-actuated membranes as part of electrically-driven implant devices, various applications can be contemplated. These include electrogenetic hormone production, optogenetic hormone production, mechanical hormone production, electro-mechanical release of drugs, electro-mechanical dosage of drugs, in-vivo micro-pumping, local in-vivo fluid/blood pumping, local in-vivo fluid/blood routing, correction of blood circulation issues of the cardiovascular system, as well as control of fibrosis and tissues passivation.

While the present invention has been described with reference to a limited number of embodiments, variants, and the accompanying drawings, it will be understood by those skilled in the art that various changes may be made, and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated.

What is claimed is:

1. An implant device, comprising:
   a cavity;
   a structure enabling a flow path between the cavity and a biological environment of the implant device;
   an actuatable membrane interposed in the flow path;
   a power-generating unit;
   a control unit connected to the power-generating unit; and
   an electromechanical system connected to both the control unit and the power-generating unit, the electromechanical system including a plurality of pairs of electrostatic actuators, wherein each pair of the plurality of pairs of electrostatic actuators is physically configured to have a comb structure that is interdigitated, and wherein the electromechanical system is further configured to vary a distance between each pair of the plurality of pairs of the electrostatic actuators of the pair upon an electrical signal applied to the electrostatic actuators in order to actuate the membrane by opening or closing micro-pores in the membrane to modify permeability of the membrane and thereby to control a transfer of substances between the cavity and the biological environment through the flow path.

2. The implant device of claim 1, wherein the electrostatic actuators deform the membrane in-plane.

3. The implant device of claim 1, wherein the electrostatic actuators deform the membrane out-of-plane.

4. The implant device of claim 3, wherein deforming the membrane out-of-plane mechanically stimulates the biological environment.

5. The implant device of claim 1, wherein the membrane includes a polymer.

6. The implant device of claim 5, wherein the polymer comprises one of:
polyvinylidene fluoride; or
polyethersulfone.

7. The implant device of claim 1, wherein the membrane is an ion-selective membrane having a surface coating configured to carry an electric charge.

8. The implant device of claim 1, further comprising a support structure, wherein the membrane is fixed at one or more locations of the support structure.

9. The implant device of claim 8, wherein the membrane is fixed to the support structure at one or more edges thereof, the implant device further includes auxiliary structures fixed to the membrane, and the electrostatic actuators of the electromechanical system are anchored to the auxiliary structures.

10. The implant device of claim 9, wherein the auxiliary structures comprise rings.

11. The implant device of claim 8, wherein the support structure includes a rectangular rim with transversal bridges, to which the membrane is attached.

12. The implant device of claim 1, wherein at least one of the pairs of electrostatic actuators is attached to the membrane in a force-fit manner on one side of the membrane.

13. The implant device of claim 1, wherein at least one of the pairs of electrostatic actuators is attached to the membrane in a force-fit manner on two sides of the membrane.

14. The implant device of claim 1, wherein the structure enabling the flow path and the membrane are jointly configured as a unidirectional valve with respect to liquid in the cavity or the biological environment.

15. The implant device of claim 1, wherein the electromechanical system is a microelectromechanical system.

16. The implant device of claim 1, wherein the electromechanical system is a nanoelectromechanical system.

17. The implant device of claim 1, wherein the cavity comprises a bioactive material.

18. The implant device of claim 1, further comprising at least one supporting layer placed on at least one side of the membrane.

19. The implant device of claim 18, wherein the at least one supporting layer induces a passive mechanical force that works against the actuation of the electromechanical system.

20. The implant device of claim 1, wherein actuation of the membrane allows external substances to enter the cavity and interact with internal substances within the cavity.

* * * * *